(12) United States Patent
Caporale et al.

(10) Patent No.: US 7,132,394 B2
(45) Date of Patent: Nov. 7, 2006

(54) PTH-LIKE PEPTIDES

(75) Inventors: Andrea Caporale, Padova (IT); Nereo Fiori, Padova (IT); Elisabetta Schievano, Padova (IT); Stefano Mammi, Padova (IT); Evaristo Peggion, Padova (IT); Michael Chorev, Chestnut Hill, MA (US); Angela Wittelsberger, Cambridge, MA (US)

(73) Assignee: Abiogen Pharma S.p.A., Ospedaletto (IT)

( * ) Notice: Subject to any disclaimer, the term of this patent is extended or adjusted under 35 U.S.C. 154(b) by 0 days.

(21) Appl. No.: 11/185,906

(22) Filed: Jul. 19, 2005

(65) Prior Publication Data
US 2006/0019902 A1    Jan. 26, 2006

(30) Foreign Application Priority Data
Jul. 19, 2004  (IT) .......................... MI2004A1440

(51) Int. Cl.
*A61K 38/08*  (2006.01)
(52) U.S. Cl. ...................................................... 514/2
(58) Field of Classification Search ................ None
See application file for complete search history.

(56) References Cited

U.S. PATENT DOCUMENTS 5,814,603 A * 9/1998 Oldenburg et al. ........... 514/12

OTHER PUBLICATIONS

Shimizu et al. "Parathyroid Hormone (PTH)-(1-14) and -(1-11) Analogs Conformationally Constrained by alpha-Aminoisobutyric Acid Mediate Full Agonist Responses via the Juxtamembrane Region of the PTH-1 Receptor" J. Biol. Chem. 2001, 276 (52), 49003-12.*
Potts "Parathyroid hormone: past and present" J. Endocrin. 2005, 187, 311-25.*

* cited by examiner

*Primary Examiner*—Cecilia J. Tsang
*Assistant Examiner*—Christina Bradley
(74) *Attorney, Agent, or Firm*—Nixon Peabody LLP

(57) ABSTRACT

The present invention relates to peptides that are parathyroid hormone (PTH) analogs, useful for the treatment of hypoparathyroidism and diseases characterized by bone mass reduction, such as osteoporosis, and for stimulating bone repair or favoring the engraftment of a bone implant; to the pharmaceutical compositions comprising these PTH-like peptides and use thereof.

10 Claims, No Drawings

PTH-LIKE PEPTIDES

The present application claims priority benefit of Italian Patent Application MI2004A001440, filed Jul. 19, 2004.

FIELD OF THE INVENTION

The present invention relates to the field of parathyroid hormone (PTH) analogs, in particular to novel PTH-like peptides hereinafter reported, useful for the treatment of hypoparathyroidism and diseases characterized by bone mass reduction, such as osteoporosis, and for stimulating bone repair or favoring the engraftment of a bone implant.

STATE OF THE ART

Parathyroid hormone (PTH) is an 84 amino acids polypeptide that acts as the most important regulator of calcium homeostasis in the human body through its direct action on bone and kidneys. The powerful anabolic effect on bone mass makes this hormone particularly interesting as potential therapeutic agent in the therapy of osteoporosis.

Unfortunately, due to the elevated molecular weight of PTH, its therapeutic applications have important limitations since its synthesis is technically difficult, and therefore expensive, and the only possible administration mode is the injection route. Moreover, PTH is easily susceptible to protease attack and must be stored at low temperature due to its low stability. In addition to these technical limitations, the toxicological data, and in particular the unfavorable results of cancerogenesis studies, induce a cautious use of PTH (Vahle J. L., *Toxicol. Pathos.* 2004 July–August, 32(4): 426–38; Whitfiel J. F., *Medscape Womens Health* 2001 Oct, 6(5):7; Kuijpers G., *BMJ* 2002 Feb. 23, 324 (7335): 435–6).

Therefore, during the last years, investigation has focused on development of PTH-derived low molecular weight peptides which have analogous biological activity but can be administered by the oral route, are protease resistant, have structural constraints that improve the interaction with the receptor, can be easily synthesized and exhibit a greater therapeutic index.

Recently, it was found that a peptide composed of the first 34 amino acids of PTH is capable of inducing receptor activation and is effective in the treatment of osteoporosis in women in menopause (Neer R. M. et al, N. Eng. J. Med. 2001, 34:1434–1441).

However, the molecular weight of this peptide is still too high for oral administration. On the other hand, lower molecular weight peptides, for instance those consisting of the first 14 or 11 amino acids of PTH (PTH(1–14) and PTH(1–11)), proved to be inactive or exhibited very low biological activity.

Recently, it was found that the activity of low molecular weight peptides can be increased by introducing particular substitutions at specific amino acid positions. For example, PTH (1–11) analogs endowed with biological activity that were described in the prior art are: [Ala$^3$, Gln$^{10}$, Arg$^{11}$]-PTH(1–11), [Ala$^3$, Gln$^{10}$, Harg$^{11}$]-PTH(1–11), and [Aib$^{1,3}$; Gln$^{10}$; Harg$^{11}$]-PTH(1–11).

All studies carried out to find low molecular weight peptides with PTH-like activity showed that the substitution of valine at position 2 with both natural or non natural amino acids, such as Aib, leads to a reduction of biological activity (*Mol. and Cell. End.*, 2000, 160 pp. 135–147; *J. Biol. Chem.* 2000, 275, pp. 21836–21843; *Endocrinology*, 2001, 142, pp. 3068–3074; *J. Biol. Chem.*, 2001, 52, pp. 49003–49012; WO 03/009804).

Therefore, these studies have generated a prejudice in the art that position 2 of PTH is essential for receptor recognition and therefore cannot be substituted when developing PTH derived low molecular weight peptides endowed with biological activity.

SUMMARY OF THE INVENTION

Now the Applicant surprisingly found that, in contrast with the prior art teachings, substitution of valine at position 2 of PTH-(1–11) does not always lead to a decrease of biological activity. In fact, the substitution of amino acid at position 2 of PTH (1–11) with α-methyl-valine or α-methyl-leucine, combined with specific substitutions of other amino acids, results in peptides which have high biological activity and stability, and are suitable for oral administration.

In one aspect, the present invention is therefore directed to a peptide with PTH-like activity, comprising an amino acid sequence selected from the group consisting of:

```
                                            (SEQ ID NO: 1)
    Ala-X2-Aib-Glu-Ile-Gln-Leu-Nle-His-Asn-Arg;

(SEQ ID NO: 2)
    Aib-X2-Ser-Glu-Ile-Gln-Leu-Nle-His-Asn-Arg;

(SEQ ID NO: 3)
    Ala-X2-Ser-Aib-Ile-Gln-Leu-Nle-His-Asn-Arg;
    and (SEQ ID NO: 4)
    Aib-X2-Aib-Glu-Ile-Gln-Leu-Nle-His-Asn-Arg,
``` wherein $X_2$ is selected from the group consisting of α-methyl-valine and α-methyl-leucine, and C- or N- derivatives thereof, and pharmaceutically acceptable salts thereof.

In another aspect, the present invention is directed to pharmaceutical compositions comprising at least one of the above said peptides, or C- or N- derivatives thereof, or pharmaceutically acceptable salts thereof.

The present invention is further drawn to a method of treating hypoparathyroidism and diseases characterized by bone mass reduction and to a method of stimulating bone repair and favoring the engraftment of a bone implant comprising administering to a patient in need of such a treatment an effective amount of at least one of the above said peptides, or a C- or N- derivative thereof, or a pharmaceutically acceptable salt thereof.

DETAILED DESCRIPTION OF THE INVENTION

According to the invention, by "Aib" the α-aminoisobutyric acid is meant, and by "Nle" norleucine is meant.

According to a particularly preferred embodiment of the present invention, $X_2$ is α-methyl-valine.

Compared to PTH (1–11) analogs known in the art, the present peptides exhibit a higher biological activity associated with greater resistance to protease degradation. The synthesis of said peptides is preferably performed by a solid phase technique, in which a resin suitable to anchor the C-terminal amino acid of the peptide is used as the solid phase. The extension of the peptide in N-terminal direction is then obtained by reaction of the amino acid bound to the resin with the next amino acid, appropriately protected usually by a FMOC or BOC group, according to a protocol that is well known to any expert in the field (Fields G. B. et al. *Int. J. Peptide and Protein Res.* 1990, 35; 161; Chone W. C. et al. *"Fmoc Solid Phase Peptide Synthesis: a practical approach"*, Oxford University Press 2000) and combines the HOBut/HBTU/Dipea activaction with the activation by means of acyl fluoride.

In fact, for steric reasons, formation of a peptide bond involving α-methyl amino acids requires the activation of the carboxyl group by means of acyl fluorides. The same activation is applied to all the residues that follow the α-methyl amino acid present in the sequence.

The peptides of the present invention have a powerful PTH-like activity and are therefore indicated for the manufacture of medicaments useful in the treatment of hypoparathyroidism and of diseases characterized by a reduction of bone mass, as for instance osteoporosis, or as adjuvants in implantology and in repair of bone fractures.

Moreover, the present peptides showed to be able to stimulate bone repair and favor the engraftment of bone implants, and can be therefore administered in a therapeutically effective dose to this aim.

Therefore the present invention refers also to pharmaceutical compositions comprising at least one of said peptides in presence of pharmaceutically acceptable excipients and/or diluents.

Said peptides are particularly suitable for oral administration. Therefore, according to a particularly preferred embodiment, the pharmaceutical compositions of the invention are formulated for oral administration, for instance in the form of tablets, capsules, granulates, drops or syrups.

The following example is given to provide a non limiting illustration of the present invention.

EXAMPLE 1

Peptide Synthesis a) Preparation and Conjugation of Resin

The RINK AMIDE MBHA resin from NOVABIOCHEM is swollen for 30' in NMP. It is filtered and the procedure is repeated for additional 30'. The resin is filtered again, then suspended in 20% piperidine solution in NMP for 45'. The resin is filtered and washed repeatedly with NMP. The resin is then suspended in NMP solution for 1 hour, with 4 equivalents of HOBt and HBTU, 8 equivalents of DIPEA. It is then filtered and washed with NMP. This procedure is followed for all amino acids that are not alpha-methylated.

b) Preparation of Acyl Fluoride 1 equivalent of amino acid protected by a Fmoc group is suspended in anhydrous $CH_2Cl_2$ and 1 equivalent of piridine is added. The temperature is brought to 0° C. and 2 equivalents of fluorocyanide are added. The temperature is allowed to rise to room temperature. After 3 hours, the reaction is stopped by addition of ice and $CH_2Cl_2$. The two phases are separated, the organic phase is washed with cold water and dried over $Na_2SO_4$. The organic solvent is removed, thus obtaining a glassy solid of white-yellow color.

An analysis of the so obtained product is performed by FT-IR spectroscopy. The acyl fluoride signal is detected at 1860–1830 $cm^{-1}$ (Carpino L. A., *J. Am. Chem. Soc.* 1990, 112, 9651).

c) Solid Phase Reaction 3 equivalents of acyl fluoride are reacted for 2 hours with 1 equivalent of DIPEA in DMF dried overnight on A4 molecular sieves (Wenschuh H., *J. Org. Chem.* 1994, 59, 3275).

The invention claimed is:

1. A peptide with PTH-like activity, comprising an amino acid sequence selected from the group consisting of:

(SEQ ID NO: 1)
Ala-X$_2$-Aib-Glu-Ile-Gln-Leu-Nle-His-Asn-Arg;

(SEQ ID NO: 2)
Aib-X$_2$-Ser-Glu-Ile-Gln-Leu-Nle-His-Asn-Arg;

(SEQ ID NO: 3)
Ala-X$_2$-Ser-Aib-Ile-Gln-Leu-Nle-His-Asn-Arg;
and (SEQ ID NO: 4)
Aib-X$_2$-Aib-Glu-Ile-Gln-Leu-Nle-His-Asn-Arg, wherein X$_2$ is a hydrophobic amino acid selected from the group consisting of α-methyl-valine and α-methyl-leucine, and pharmaceutically acceptable salts thereof.

2. The peptide according to claim 1, wherein X$_2$ is (α-methyl-valine.

3. A pharmaceutical composition comprising a therapeutically effective amount of at least a peptide, or a pharmaceutically acceptable salt thereof as defined in claim 1, in presence of pharmaceutically acceptable excipients and/or diluents.

4. The pharmaceutical composition according to claim 3, formulated for oral administration.

5. The pharmaceutical composition according to claim 4, in the form of tablets, capsules, granulates, tablets, drops or syrups.

6. The pharmaceutical composition according to claim 3, for use in the treatment of hypoparathyroidism and diseases characterized by bone mass reduction or for the repair of bone fractures.

7. The pharmaceutical composition according to claim 6, wherein said disease characterized by bone mass reduction is osteoporosis.

8. A method of treating hypoparathyroidism and diseases characterized by bone mass reduction comprising administering to a patient in need of such a treatment an effective amount of at least a peptide, or a pharmaceutically acceptable salt thereof as defined in claim 1.

9. The method according to claim 8, wherein said disease characterized by bone mass reduction is osteoporosis.

10. A method of stimulating bone repair or favoring the engraftment of a bone implant comprising administering to a patient in need of such a treatment an effective amount of at least a peptide, or a pharmaceutically acceptable salt thereof as defined in claim 1.

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Artificial sequence
<220> FEATURE:
<223> OTHER INFORMATION: PTH(1-11)-like peptide
<220> FEATURE:
<221> NAME/KEY: MISC_FEATURE
<222> LOCATION: (2)..(2)
<223> OTHER INFORMATION: X is alpha-methyl valine or alpha-methyl
      leucine
<220> FEATURE:
<221> NAME/KEY: MISC_FEATURE
<222> LOCATION: (3)..(3)
<223> OTHER INFORMATION: X is Aib (i.e. alpha-aminoisobutyric acid)
<220> FEATURE:
<221> NAME/KEY: MISC_FEATURE
<222> LOCATION: (8)..(8)
<223> OTHER INFORMATION: X is NLE (i.e. norleucine)

<400> SEQUENCE: 1

Ala Xaa Xaa Glu Ile Gln Leu Xaa His Asn Arg
1               5                   10

<210> SEQ ID NO 2
<211> LENGTH: 11
<212> TYPE: PRT
```

```
<213> ORGANISM: Artificial sequence
<220> FEATURE:
<223> OTHER INFORMATION: PTH(1-11)-like peptide
<220> FEATURE:
<221> NAME/KEY: MISC_FEATURE
<222> LOCATION: (1)..(1)
<223> OTHER INFORMATION: X is Aib (i.e. alpha-aminoisobutyric acid)
<220> FEATURE:
<221> NAME/KEY: MISC_FEATURE
<222> LOCATION: (2)..(2)
<223> OTHER INFORMATION: X is alpha-methyl valine or alpha-methyl
      leucine
<220> FEATURE:
<221> NAME/KEY: MISC_FEATURE
<222> LOCATION: (8)..(8)
<223> OTHER INFORMATION: X is norleucine

<400> SEQUENCE: 2

Xaa Xaa Ser Glu Ile Gln Leu Xaa His Asn Arg
1               5                   10

<210> SEQ ID NO 3
<211> LENGTH: 11
<212> TYPE: PRT
<213> ORGANISM: Artificial sequence
<220> FEATURE:
<223> OTHER INFORMATION: PTH(1-11)-like peptide
<220> FEATURE:
<221> NAME/KEY: MISC_FEATURE
<222> LOCATION: (2)..(2)
<223> OTHER INFORMATION: X is alpha-methyl valine or alpha-methyl
      leucine
<220> FEATURE:
<221> NAME/KEY: MISC_FEATURE
<222> LOCATION: (4)..(4)
<223> OTHER INFORMATION: X is Aib (i.e. alpha-aminoisobutyric acid)
<220> FEATURE:
<221> NAME/KEY: MISC_FEATURE
<222> LOCATION: (8)..(8)
<223> OTHER INFORMATION: X is norleucine

<400> SEQUENCE: 3

Ala Xaa Ser Xaa Ile Gln Leu Xaa His Asn Arg
1               5                   10

<210> SEQ ID NO 4
<211> LENGTH: 11
<212> TYPE: PRT
<213> ORGANISM: Artificial sequence
<220> FEATURE:
<223> OTHER INFORMATION: PTH(1-11)-like peptide
<220> FEATURE:
<221> NAME/KEY: MISC_FEATURE
<222> LOCATION: (1)..(1)
<223> OTHER INFORMATION: X is Aib (i.e. alpha-aminoisobutyric acid)
<220> FEATURE:
<221> NAME/KEY: MISC_FEATURE
<222> LOCATION: (2)..(2)
<223> OTHER INFORMATION: X is alpha-methyl valine or alpha-methyl
      leucine
<220> FEATURE:
<221> NAME/KEY: MISC_FEATURE
<222> LOCATION: (3)..(3)
<223> OTHER INFORMATION: X is Aib (i.e. alpha-aminoisobutyric acid)
<220> FEATURE:
<221> NAME/KEY: MISC_FEATURE
<222> LOCATION: (8)..(8)
<223> OTHER INFORMATION: X is norleucine

<400> SEQUENCE: 4

Xaa Xaa Xaa Glu Ile Gln Leu Xaa His Asn Arg
1               5                   10
```